United States Patent
Zhu

(10) Patent No.: US 10,912,584 B2
(45) Date of Patent: Feb. 9, 2021

(54) TROCAR SEAL MEMBRANE COMPRISING MULTI-DIMENSIONAL PLEATS

(71) Applicant: 5RMED TECHNOLOGY(CHENGDU) CO., LTD., Chengdu (CN)

(72) Inventor: Moshu Zhu, Chengdu (CN)

( * ) Notice: Subject to any disclaimer, the term of this patent is extended or adjusted under 35 U.S.C. 154(b) by 146 days.

(21) Appl. No.: 16/249,893

(22) Filed: Jan. 16, 2019

(65) Prior Publication Data
US 2019/0142458 A1 May 16, 2019

Related U.S. Application Data

(63) Continuation of application No. PCT/CN2017/093603, filed on Jul. 20, 2017.

(51) Int. Cl.
*A61B 17/34* (2006.01)
*A61M 39/06* (2006.01)

(52) U.S. Cl.
CPC ...... *A61B 17/3439* (2013.01); *A61B 17/3462* (2013.01); *A61B 17/3498* (2013.01); *A61B 2017/347* (2013.01); *A61B 2017/3464* (2013.01); *A61M 2039/0633* (2013.01)

(58) Field of Classification Search
CPC .............. A61B 17/3462; A61M 39/06; A61M 2039/0626; A61M 2039/0686; A61M 2039/0633; A61M 2039/0653; A61M 2039/0673; A61M 2039/064; A61M 2039/0646; A61M 39/0606
See application file for complete search history.

(56) References Cited

U.S. PATENT DOCUMENTS 5,827,228 A * 10/1998 Rowe ................. A61B 17/3417
604/167.02
7,112,185 B2 9/2006 Hart et al.
7,591,802 B2 9/2009 Johnson et al.
(Continued)

FOREIGN PATENT DOCUMENTS

CN 101478924 A 7/2009
CN 101480354 A 7/2009
(Continued)

OTHER PUBLICATIONS

Internation Search Report of PCT/CN2017/093603, dated Sep. 27, 2017.

*Primary Examiner* — Emily L Schmidt
(74) *Attorney, Agent, or Firm* — Erson IP (Nelson IP)

(57) ABSTRACT

A trocar seal membrane with multi-dimensional pleats. The seal membrane includes a proximal opening, a distal aperture, and a sealing wall extending from the distal aperture to the proximal opening, the sealing wall includes a proximal surface and a distal surface. The distal aperture formed by a sealing lip for accommodating the inserted instrument forms a gas-tight seal. In the lip-adjacent area, the sealing wall simultaneously has a plurality of transverse pleats extending laterally outwardly from the sealing lip and a plurality of tangential pleats uniformly distributed around the sealing lip. The pleated sealing wall can enlarge hoop circumference in the lip-adjacent area, and reduce overall deformation when a large-diameter instrument is inserted, thereby reducing friction and improving sealing reliability.

13 Claims, 10 Drawing Sheets

(56) References Cited

U.S. PATENT DOCUMENTS

| | | |
|---|---|---|
| 7,789,861 B2 | 9/2010 | Franer |
| 7,842,014 B2 | 11/2010 | Schweitzer et al. |
| 2005/0203467 A1 | 9/2005 | O'Heeron et al. |
| 2005/0288634 A1 | 12/2005 | O'Heeron et al. |
| 2007/0255218 A1* | 11/2007 | Franer ............... A61B 17/3462 604/167.02 |
| 2009/0082735 A1* | 3/2009 | Schweitzer ........ A61B 17/3462 604/167.01 |
| 2009/0326467 A1 | 12/2009 | Bettuchi et al. |
| 2010/0179479 A1 | 7/2010 | Albrecht et al. |

FOREIGN PATENT DOCUMENTS

| | | |
|---|---|---|
| CN | 102764150 A | 11/2012 |
| CN | 205126367 U | 4/2016 |
| CN | 105997204 A | 10/2016 |
| CN | 206434393 U | 8/2017 |
| EP | 0994740 A1 | 4/2000 |
| EP | 2452639 A1 | 5/2012 |

\* cited by examiner

TROCAR SEAL MEMBRANE COMPRISING MULTI-DIMENSIONAL PLEATS

CROSS-REFERENCE TO RELATED APPLICATIONS

This application is a continuation of International Patent Application No. PCT/CN2017/093603 with a filing date of Jul. 20, 2017, designating the United States, now pending, and further claims priority to Chinese Patent Application No. 201610625807.0 with a filing date of Aug. 2, 2016. The content of the aforementioned applications, including any intervening amendments thereto, are incorporated herein by reference.

TECHNICAL FIELD

The present invention relates to a minimally invasive surgical instrument, and in particular, to a trocar sealing element.

BACKGROUND OF THE PRESENT INVENTION

A trocar is a surgical instrument, that is used to establish an artificial access in minimally invasive surgery (especially in rigid endoscopy). Trocars comprise in general a cannula and an obturator. The surgical use of trocars generally known as: first make the initial skin incision at the trocar insertion site, then insert the obturator into the cannula, and then together they facilitated penetration of the abdominal wall through incision into the body cavity. Once penetrated into the body cavity, the obturator is removed, and the cannula will be left as access for the instrument get in/out of the body cavity.

In rigid endoscopy surgery, it is usually necessary to establish and maintain a stable pneumoperitoneum for the sufficient surgical operation space. The cannula comprises a sleeve, an outer body, a seal membrane (also known as instrument seal) and a duck bill (also known as closure valve). Said cannula providing a channel for the instrumentation in/out of the body cavity, said outer body connecting the sleeve, the duck bill and the seal membrane into a sealing system; said duck hill normally not providing sealing for the inserted instrument, but automatically closing and forming a seal when the instrument is removed; said seal membrane accomplishing a gas-tight seal against the instrument when it is inserted.

In a typical endoscopic procedure, it is usually set up 4 trocars (access), i.e. 2 sets of small diameter cannula (normally 5 mm in diameter), and 2 sets of large diameter cannula (normally 10~12 mm in diameter). Instruments, in general passing through a small cannula are only for ancillary works; herein one large cannula as an endoscope channel, and the other large cannula as the main channel for surgeon to perform surgical procedures. Through said main channel thereof, 5 mm diameter instruments used in approximately 80% of the procedure, and said large cannula used in approximately 20% of the procedure; furthermore, 5 mm instruments and large diameter instruments need to be switched frequently. The small instruments are mostly used, so that the sealing reliability of which is more important. The large instruments are more preferably used in a critical stage of surgery (Such as vascular closure and tissue suturing), therein switching convenience and operational comfort are more important.

FIG. 1 and FIG. 2 depict a typical 12 mm diameter cannula 700. Said cannula 700 comprises a lower housing 710, an upper housing 720, a seal membrane 730 which sandwiched between the lower housing 710 and the upper housing 720, and a duckbill seal 750. Said lower housing 710 including center hole 713 defined by an elongated tube 711. Said upper housing 720 including the proximal hole 723 defined by the inner wall 721. Said membrane 730 including a proximal opening 732, a distal aperture 733, a sealing lip 734, a frustum sealing wall 735, a flange 736 and an outer floating portion 737. Said distal opening 733 formed by a sealing lip 734. Said sealing lip 734 defining a longitudinal axis 741, transverse plane 742 substantially perpendicular to said axis 741; define the angle between the rotary-generating line (or generatrix) of the frustum sealing wall 735 and the transverse plane 742 as a guide angle ANG1.

As illustrated in FIG. 1, when a 5 mm diameter instrument inserted, it is approximately considered that only hoop force generated by the deformation of the sealing lip 734, ensures a reliable seal for the instrument. It is nevertheless favorable to operate the instrument from various extreme angles in surgery. There's a lot space left for the 5 mm diameter instrument to move radially in the 12 mm diameter cannula, so that greater radial force would be taken by the sealing lip 734. Therefore, the sealing lip 734 should have sufficient hoop force for the inserted 5 mm diameter instrument to ensure its sealing reliability thereof.

As illustrated in FIG. 2, drawing a cylinder of Di (Di>5 mm) to cut the sealing wall 735 forms an intersecting line 738. It is easy to understand for those skilled in the art, when an Di diameter instrument is inserted, the strain (stress) of said sealing wall 735 in the area from the sealing lip 734 to the intersecting line 738 will be larger, so the area refer to as lip-adjacent area (or concentration stress area). While the strain (stress) of said sealing wall 735 from the intersecting line 738 to the flange 736 is small. However, the different diameter (Di value) makes the boundary range of the lip-adjacent area (or concentration stress area) change larger or smaller. For the convenience of quantification, it is defined when Di is designed as the maximum diameter of the surgical instrument passing through the seal membrane, the area from the sealing lip 734 to the intersection line 738 is the lip-adjacent area.

As illustrated in FIG. 3, when a large diameter instrument is inserted (e.g. 12.8 mm), the sealing lip 734 will expand to a suitable size to accommodate the inserted instrument; said sealing wall 735 is divided into two portions: a conical wall 735c and a cylindrical wall 735d; said cylindrical wall 735d wrapped around the outer surface of the instrument to form a wrapped area with a high concentration of stress. Defining the intersecting line of the conical wall 735c and the cylindrical wall 735d as intersecting line 738a. When the instrument is removed, said sealing wall 735 return to natural state, and said intersecting line 738a spring-back to a ring radius of Dx, defined as intersecting line 738b, (not shown in FIG.); said intersecting line 738b is a bending boundary line when inserting a large diameter instrument. The angle between the rotary generating line of said conical wall 735c and the transverse plane 742 defines as ANG2, ANG2>ANG1; that is, when the large-diameter instrument is inserted, said sealing wall 735 rotates and stretch around its intersection line of said flange 736. Defining the height of the cylindrical wall 735d as Ha, not a fixed value; the factors such as different size of said distal aperture, different size of said sealing lip, different thickness of said sealing wall, different said guide angle or different diameter of inserted instrument, make Ha different.

The instrument inserted into the sealing membrane and moved during surgical procedure, there is large frictional resistance between the wrapped area and the inserted instrument. Said large frictional resistance is normally easy to cause the seal inversion, poor comfort of performance, fatigue performance, even result in cannula insecurely fixed on the patient's abdominal wall etc., such that the performance of cannula assembly is affected.

Among the defects caused by the large frictional resistance, the seal inversion is one of the most serious problems that affecting the performance of the cannula. As illustrated in FIG. 4, when a large diameter instrument is removed, easily cause seal inversion. When inversion happened, said sealing wall 735 divided into a cylindrical wall 735e, a conical wall 735f, and a conical wall 735g; said cylindrical wall 735e wrapped around the outer surface of the instrument to form a wrapped area with a high concentration of stress. Defining the height of the cylindrical wall 735e to be Hb, normally Hb>Ha; that is, the frictional resistance when the instrument is removed greater than it when the instrument is inserted, this difference affects the surgeon's operating feeling and even make the surgeon confused. More seriously, the inversion of the seal membrane may stretch into the proximal hole 723, that is the seal membrane positioned between the instrument and the inner wall 721 gets completely jammed. Measures for preventing the seal inversion are respectively disclosed in U.S. Pat. Nos. 7,112,185 and 7,591,802, and those measures can effectively reduce the probability of inversion but not completely solve the problem.

The simplest way to reduce the frictional resistance is reducing the coefficient of friction between the two contacting surfaces with grease but the reliability of this way is not good. During procedures, due to instruments long-term repeated scraping with the seal membrane and repeated switching, it is easy to erase the grease off and carried away, resulting in bad lubrication.

A protector assembly adjoined by a seal membrane is disclosed in U.S. Pat. No. 5,342,315. Said protector to permit the sharp edge of the instrument to pass through the opening in the seal membrane without causing damage to the seal membrane, and the surface friction coefficient of the protector assembly is smaller than the surface friction coefficient of the seal membrane, which results in less frictional drag, but the lip-adjacent area is normally not completely covered by the protector assembly.

A seal member with ribs is disclosed in U.S. Pat. No. 5,827,228 that is a plurality of spaced ribs provided to extend outwardly from center hole to reduce surface contact between the inserted instrument and the seal member, and thereby reducing the frictional resistance, a similar ribs which disclosed in EP0994740 also reducing surface contact and strengthen the tensile of the seal member oriented to axial.

A sealing element comprising a flexible wall closed annularly with the edges foldable in a wave-like manner is disclosed in U.S. Pat. No. 7,842,014, wherein the wall bears, a wave-like sealing lip and is a wavy pleated seal body, in such manner it can enlarge hoop circumference, and reduce the hoop force to a certain extent.

Chinese invention application CN101480354A (currently rejected) discloses a seal member containing an easily deformable groove, wherein is characterized in that it has a plurality of easily deformable grooves on the conical surface of the seal member from the sealing lip; said the thickness of the deformable groove wall is much smaller than the thickness of the conical surface wall, primary take advantage of the elongation of the deformable groove to accommodate the inserted large diameter instrument.

Although, in the prior art many solutions for reducing the frictional resistance have been disclosed, these solutions basically only propose measures from one certain factor affecting frictional resistance, the effect of which is small or not obvious. Some modifications solved a certain defects may lead to cause another bug. Such as, reinforcing ribs on the seal membrane to reduce surface contact, meanwhile strengthen the tensile of the seal membrane; or a deformable groove with a thickness much smaller than that of a truncated conical surface can cause the deformable groove to be easily damaged; due to the adoption a said wave-like sealing lip which enlarge hoop circumference, the sealing reliability will be sacrificed when a 5 mm diameter instrument is inserted, if the wave-like sealing lip is used but without enlarge hoop circumference, the wave-like sealing lip will lose its improvement effect. In summary there are many factors affecting the frictional resistance, and the comprehensive effects of various factors must be considered in the perspective of mechanics and tribology.

The seal membrane is preferably produced from rubber such as natural rubber, silicone or polyisoprene, its mechanical properties including super elastic and viscoelastic. Although the mechanical model of the rubber deformation process is complicated, it can still apply the generalized Hooke's law to describe approximatively its elastic behavior; and Newton's internal friction law to describe the viscous behavior. Research suggests that the main factors affecting the friction of the two surfaces in contact between the rubber and the instrument include: the smaller the friction coefficient of said two surfaces, the smaller the friction is; the better lubrication condition of said two surfaces in contact, the friction smaller is; the smaller normal pressure of said two surfaces, the friction smaller is. Comprehensively considering the above factors, the present invention proposes better solutions for reducing the frictional resistance between the seal membrane and the inserted instrument.

In addition to said frictional resistance greatly affecting the performance of the cannula assembly, the stick-slip of the seal membrane is another main factor affecting the performance of trocar. Said stick-slip means that when the instrument moves longitudinally in the sleeve, the sealing lip and lip-adjacent area sometimes are relatively statically attached to the instrument (at this point, the friction between the instrument and the seal membrane is mainly static friction); but sometimes it produced a relatively slippery phenomenon with the instrument (at this point, the friction between the instrument and the seal membrane is mainly dynamic friction.); and said static friction is much greater than said dynamic friction. The two frictions alternately occur, which causes the movement resistance and speed of the instrument in the seal membrane to be unstable. It is easy to be understand for those skilled in the art, that in minimally invasive surgery the surgeon can only use surgical instruments to touch (feel) the patient's organs, and observe a part of the working head of the instruments through endoscopic image system. In this case where the vision is limited and it cannot be touched, the surgeon typically uses the feedback of the resistance when moving instruments as one of the information to judge whether the operation is abnormal nor not. The stick-slip affects the comfort of operation, the accuracy of positioning, and even induces the surgeon to make false judgment.

During the surgical application of the cannula, the stick-slip is difficult to avoid, but can be reduced. Researches have shown that said stick-slip is affected by two main factors: one is that the smaller the difference between the maximum static friction and the dynamic friction, the weaker the stick-slip is; the other is that the larger the axial tensile stiffness of the seal membrane, the weaker the stick-slip is. Avoiding excessive the hoop force between the seal membrane and the instrument, reducing the two surfaces contacted, maintaining good lubrication, respectively, can reduce the difference between the maximum static friction and the dynamic friction, thereby reducing stick-slip, meanwhile, increasing the axial tensile stiffness of the seal membrane also helps to reduce the stick-slip phenomenon. The invention also proposes measures for improving stick-slip.

In summary, so far, there is no cannula that can effectively solve the said problems.

SUMMARY OF PRESENT INVENTION

In conclusion, one object of the invention is to provide a trocar seal membrane with multi-dimensional pleats, said seal membrane comprises a proximal opening, a distal aperture, and a sealing wall from, the distal aperture extending to the proximal opening, said the sealing wall including a proximal surface and a distal surface; said distal aperture are formed by a sealing lip for accommodating the inserted instrument and forming a gas-tight seal. In the lip-adjacent area, the sealing wall simultaneously has a plurality of transverse pleats extending laterally outwardly from the sealing lip and a plurality of tangential pleats uniformly distributed around the sealing lip.

Preferably, said sealing wall further comprises a solid-rib extending laterally outward from the sealing lip.

Preferably, said sealing wall further comprises reverse concave-channels extending laterally outward from the sealing lip and recessing from the distal surface of said sealing wall to the proximal surface, the opening of reverse concave-channels towards the distal surface. From the perspective of the distal surface, the reverse concave-channel is a hollow convex-rib raised from the proximal surface and which comprises 2 plane side-walls without pleats.

Preferably, the section of said tangential pleats is U-shaped.

Preferably, the section of said tangential pleats is V-shaped.

Preferably, wherein there are 4 said reverse concave-channels.

Preferably, said sealing lip is circular or cylindrical.

Preferably, said seal membrane further comprises a flange that intersects the multi-dimensional pleats and the reverse concave-channels simultaneously, and a floating portion with a plurality of transverse pleats extending from the flange to the proximal opening.

Another object of the invention is to provide a trocar seal assembly, which including a lower retainer ring, an upper retainer ring, a protection device, an upper body and a upper cover; said seal membrane includes a flange simultaneously intersects said pleats and said ribs, and an outer floating portion including at least one transverse pleat extending from the flange to the proximal opening. And said proximal opening are sandwiched between the upper housing and the upper cover.

As described in the background, the wrapped area formed by the sealing lip and the lip-adjacent area when a large diameter instrument inserted, is the major factor cause of frictional resistance. For reducing said frictional resistance, comprehensive consideration should be given such as reducing the radial stress between the instrument and the seal membrane, reducing said wrapped area, and reducing the actual contact area of the two surfaces. It is easy to understand for those skilled in the art that in accordance with the generalized Hooke's law and Poisson effect, enlarge hoop circumference, and reduce hoop strain (stress), thereby reducing radial strain (stress). But it should be noted that it is impossible to enlarging the hoop circumference in order to reduce the strain of the sealing lip which will result in reduced sealing reliability when applying 5 mm instruments. Since the stress in the lip-adjacent area is highly concentrated when applying a large diameter instrument, the hoop circumference of the lip-adjacent area should be rapidly increased. In regard to outside the lip-adjacent area, since the strain (stress) is small, it is not necessary to adopt measures to enlarge the hoop circumference. In addition, enlarging the hoop circumference, in the meantime increasing the axial tensile stiffness in the lip-adjacent area, thereby the stick-slip in the lip-adjacent area is improved.

In one aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal. In the lip-adjacent area, the sealing wall simultaneously has a plurality of transverse pleats extending laterally outwardly from the sealing lip and a plurality of tangential pleats uniformly distributed around the sealing lip. The pleated sealing wall can enlarge hoop circumference in the lip-adjacent area, and reduce overall deformation when a large diameter instrument is inserted, thereby reducing friction and improving sealing reliability.

In another aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted, instrument forms a gas-tight seal. In the lip-adjacent area, the sealing wall simultaneously has a plurality of transverse pleats extending laterally outwardly from the sealing lip and a plurality of tangential pleats uniformly distributed around the sealing lip. Said sealing wall further comprises a solid-rib extending laterally, outward from the sealing lip, said solid-rib increasing the axial tensile stiffness in the lip-adjacent area, thereby improving stick-slip.

In another aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal. In the lip-adjacent area, the sealing wall simultaneously has a plurality of transverse pleats extending laterally outwardly from the sealing lip and a plurality of tangential pleats uniformly distributed around the sealing lip. Said sealing wall further comprises reverse concave-channels extending laterally outward from the sealing lip and recessing from the distal surface of said sealing wall to the proximal surface, the opening of reverse concave-channels towards the distal surface. From the perspective of the proximal surface, the reverse concave-channel is a hollow convex-rib raised from the proximal surface and which comprises 2 plane side-walls without pleats. The section of said tangential pleats is V-shaped; the section of said reverse concave-channels is U-shaped; said sealing lip is cylindrical. Said seal membrane further comprises a flange that simultaneously intersects said transverse pleats, said tangential pleats and said reverse concave-channels, and an outer floating portion with a plurality of transverse pleats extending from the flange to the proximal opening. Said pleated sealing wall and said reverse concave-channels can enlarge hoop circumference in the lip-adjacent area, and reduce friction. And said reverse concave-channels increase the axial tensile stiffness in the lip-adjacent area, thereby improving stick-slip.

In another aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing lip for accommodating the inserted instrument forms a gas-tight seal. The sealing wall simultaneously has a plurality of transverse pleats extending laterally outwardly from the sealing lip and a plurality of tangential pleats uniformly distributed around the sealing lip, said sealing wall further comprises reverse concave-channels extending laterally outward from the sealing lip and recessing from the distal surface of said sealing wall to the proximal surface, the opening of reverse concave-channels towards the distal surface. From the perspective of the proximal surface, the reverse concave-channel, is a hollow convex-rib raised from the proximal surface and which comprises 2 plane side-walls without pleats. The section of said tangential pleats is V-shaped; the section of said reverse concave-channels is U-shaped; said sealing lip is circular. Said pleated sealing wall and said reverse concave-channels can enlarge hoop circumference in the lip-adjacent area, and reduce friction. And said reverse concave-channels increase the axial tensile stiffness in the lip-adjacent area, thereby improving stick-slip.

Another object of the invention is to provide a trocar seal assembly, which including a lower retainer ring, a seal membrane, a protection device, an upper retainer ring, an upper body and an upper cover. Said the seal membrane and said protection device are sandwiched between the lower retainer ring and the upper retainer ring, said protection device permit the sharp edge of the instrument to pass through without causing perforations or tears to the seal membrane; the proximal opening of which is sandwiched between said upper body and said upper cover, and said outer floating portion makes said seal membrane and protector float laterally in the housing formed by the upper body and the cover.

It is believed that the above invention or other objects features and advantages, will be understood with the drawings and detailed description.

DESCRIPTION OF THE DRAWINGS

A more complete appreciation of this invention, and many of the attendant advantages thereof will be readily apparent as the same becomes better understood by reference to the following detailed description, where.

In all views, the same referred number shows the same element or assembly.

DETAILED DESCRIPTION OF PREFERRED EMBODIMENTS

Embodiments of the invention are disclosed herein, however, it should be understood that the disclosed embodiments are merely examples of the invention, which may be implemented in different ways. Therefore, the invention is not intended to be limited to the detail shown, rather, it is only considered as the basis of the claims and the basis for teaching those skilled in the art how to use the invention.

Figure 1:
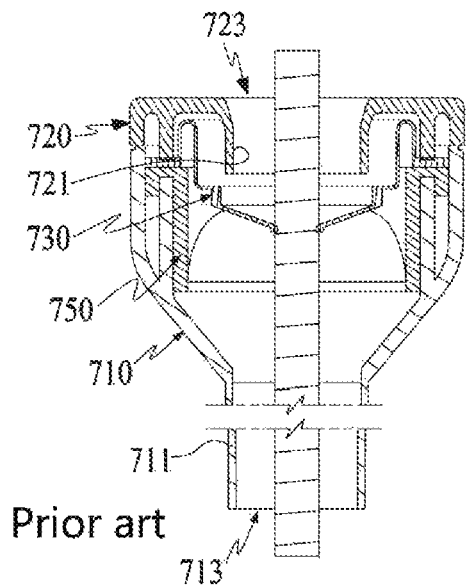
FIG. 1: shows a simulated distorted view of the cannula with the 5 mm diameter instrument inserted in the prior art.
Figure 2:
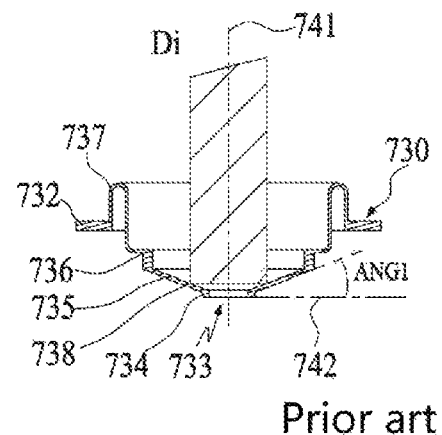
FIG. 2: shows a detailed view of the seal membrane 730 in the prior art.
Figure 3:
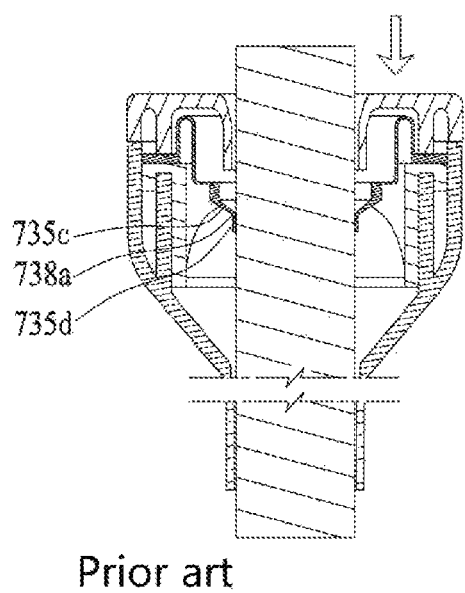
FIG. 3: shows a simulated distorted view of the cannula with the 12.8 mm diameter instrument inserted in the prior art.
Figure 4:
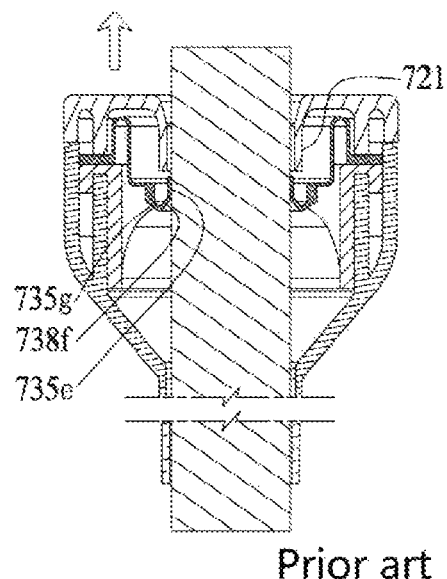
FIG. 4: shows a simulated distorted view of the cannula with the 12.8 mm diameter instrument removed in the prior art.
Figure 5:
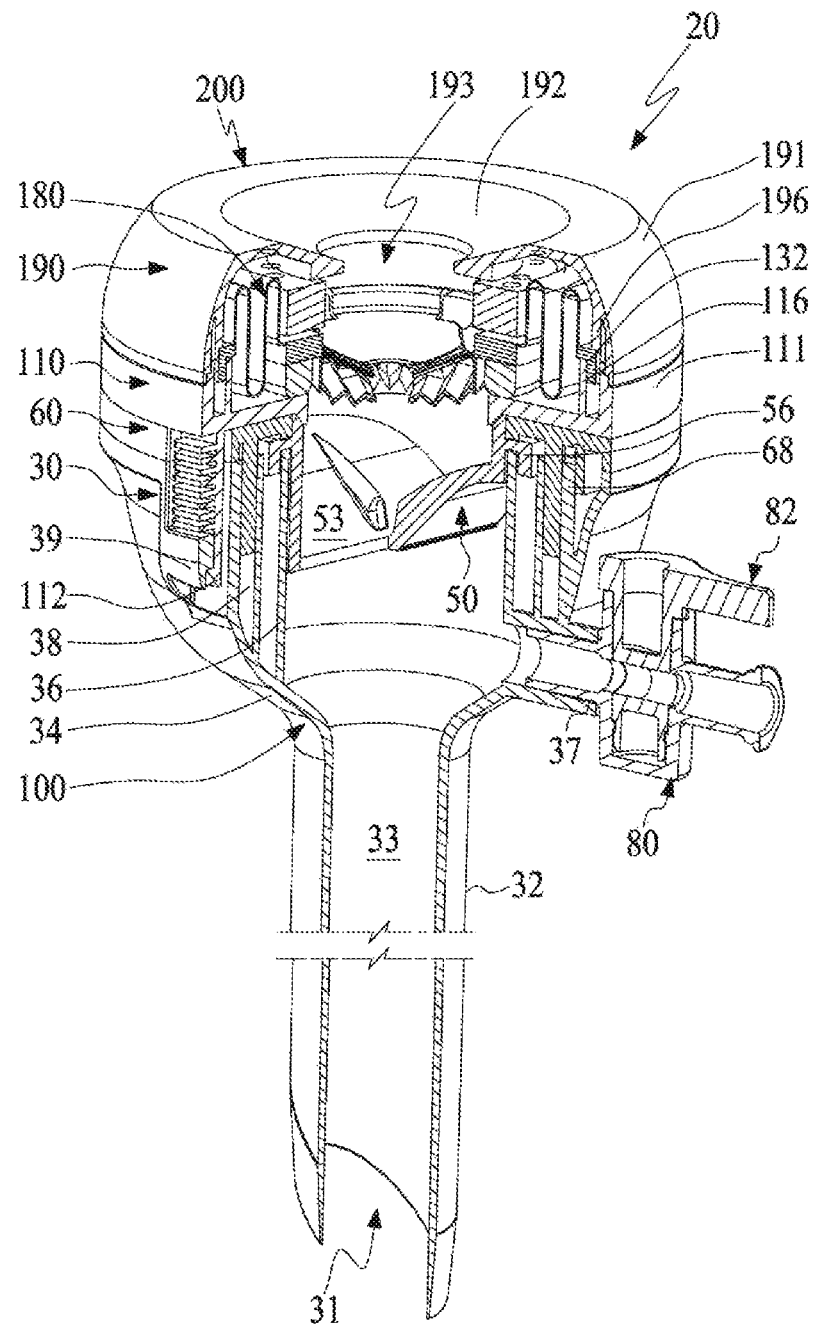
FIG. 5: shows a 3D perspective partial sectional view of the cannula in the invention.

FIG. 5 shows an overall view of the structure of trocar. A typical trocar comprises an obturator 10 (not shown) and a cannula 20. The cannula 20 comprises an open proximal end 192 and an open distal end 31. In a typical embodiment, said obturator 10 passes through said cannula 20, together they facilitated penetration of the abdominal wall through incision into the body cavity. Once penetrated into the body cavity, the obturator 10 is removed, and the cannula 20 will be left as access for the instrument get in/out of the body cavity. Said proximal end 192 in the external position of the patient and said distal end 31 in the internal position. A preferred cannula 20 can be divided into the first seal assembly 100 and the second seal assembly 200. Locking receptacle 39 in said seal assembly 100 can be locked with snap-in projection 112 in said seal assembly 200. The cooperation of snap-in projection 112 and the locking receptacle 39 can be quick release by one hand. The main purpose is for convenience of taking out tissues or foreign matter from the patient in the surgery. There are multiple ways to implement the quick, release connection of said seal assembly 100 and assembly 200. In addition to the structure shown in this embodiment, a threaded connection, a rotary snap-in or other quick lock structure also may be applied. Alternatively, said assembly 100 and assembly 200 can be designed as a structure that can not be split quickly.

FIG. 5 shows the composition and assembly relationship of the first seal assembly 100. The lower body 30 includes an elongated tube 32, which defines the sleeve 33 passed through the distal end 31 and is connected to the outer housing 34. Said lower body 30 comprises an inner wall 36 supporting duck bill seal and a valve bore 37 that communicates with the inner wall 36. The plunger 82 mounted in the valve body 80, the said two are mounted into said valve bore 37. The flange 56 of the duck bill seal 50 is sandwiched between the inner wall 36 and the lower cover 60. There are various ways of fixing between the lower cover 60 and the lower body 30, such as the interference fit, ultrasonic welding, glue bonding, and snap fastening. 4 cylinders 68 of said lower cover 60, in this embodiment, 4 holes 38 of said lower body 30 are adopted to interference fit, so that the duckbill seal 50 is in the compressed state. Said tube 32, said the inner wall 36, said duck bill seal 50, said valve body 80 and said plunger 82 together are comprised the first chamber. Said duck bill seal 50, in this embodiment, is a single-slit, while other types of closure valves may also be used, including flapper valves, multi-silted duck bill valves. When the instrument is passed through said duck bill seal 50, the duckbill 53 will be opened, but it generally does not provide a complete seal against the instrument. When the instrument is removed, said duckbill 53 closed and substantially prevents insufflation fluid from escaping through the first chamber.

FIG. 5 shows the composition and assembly relationship of the second seal assembly 200. The seal membrane assembly 180 is sandwiched between the upper cover 110 and the upper body 190. The proximal end 132 of the seal membrane assembly 180 is secured between the inner ring 116 of the upper cover 110 and the inner ring 196 of the upper body 190. There are various secured ways between the upper cover 190 and the upper body 110, such as the interference fit, ultrasonic welding, glue bonding, and snap fastening. The connection method, shown in this embodiment, is the outer shell 191 of the upper body 190 and the outer shell 111 of the upper cover 110 are secured by ultrasonic welding, so that the proximal end 132 of the seal membrane assembly 180 is in the compressed state. The center hole 113 of said upper cover 110, said inner ring 116, and said seal membrane assembly 180 together are comprised the second chamber.

Figure 6:
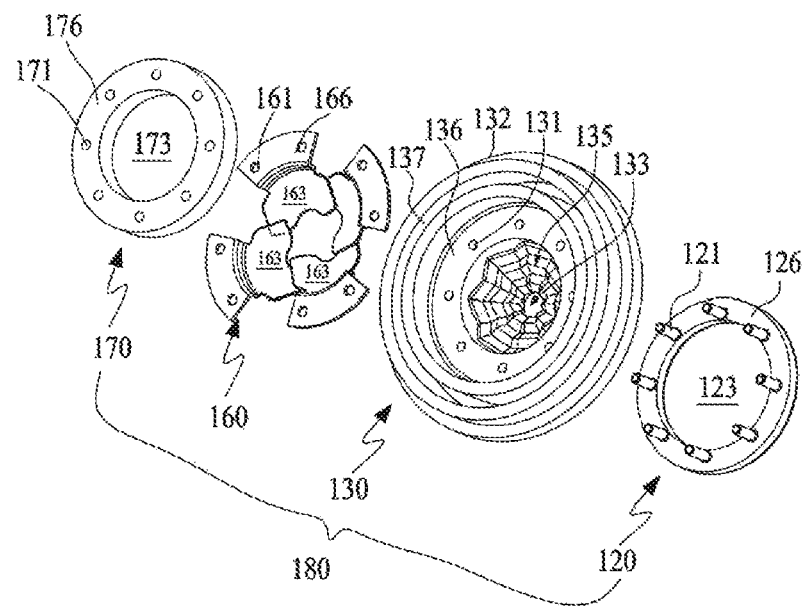
FIG. 6: shows an exploded view of the seal membrane assembly of the cannula in FIG. 5.
Figure 7:
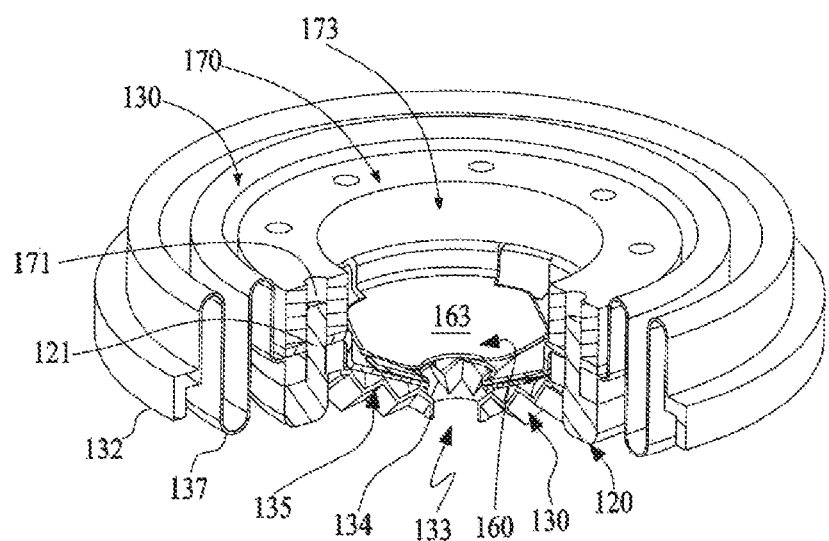
FIG. 7: shows a 3D perspective partial sectional view of the seal membrane assembly in FIG. 6.
Figure 8:
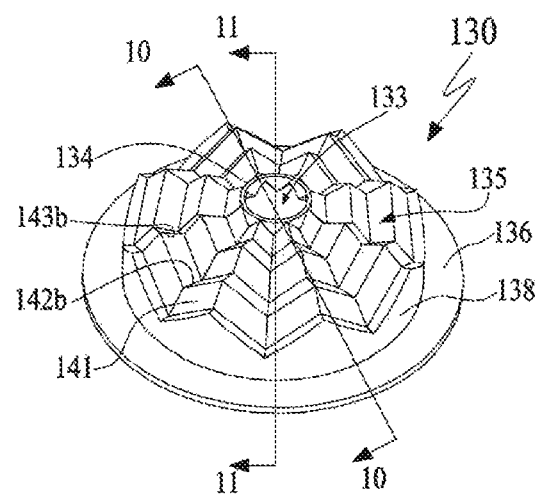
FIG. 8: shows a 3D perspective view of the seal membrane without the proximal end and floating portion in FIG. 6.
Figure 9:
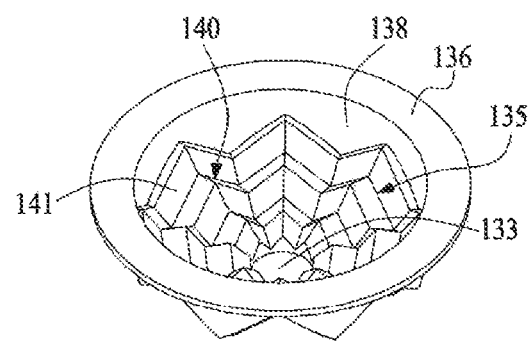
FIG. 9: shows a 3D perspective reserve sectional view of the seal membrane in FIG. 8.
Figure 10:
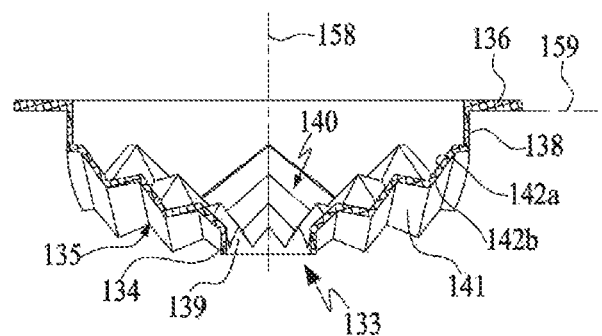
FIG. 10: shows a sectional view along line 10-10 in FIG. 9.
Figure 11:
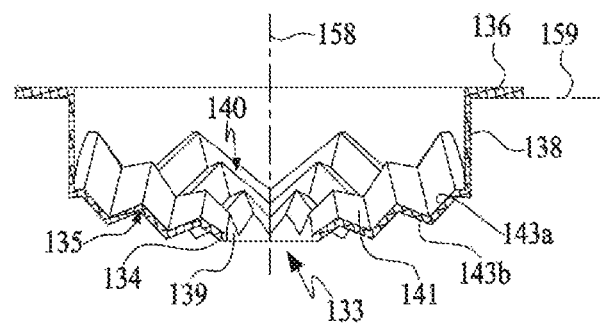
FIG. 11: shows a sectional view along line 11-11 in FIG. 8.
Figure 12:
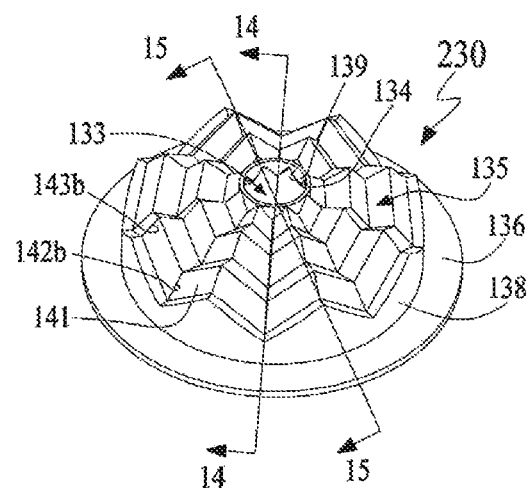
FIG. 12: shows a 3D perspective view of the seal membrane assembly in the second embodiment.
Figure 13:
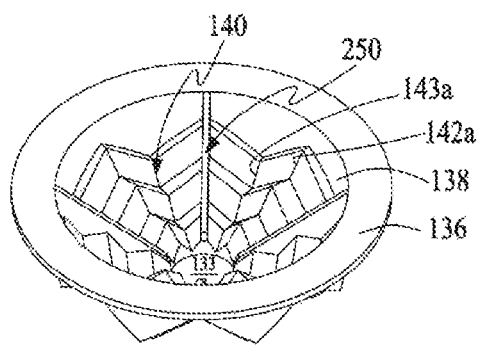
FIG. 13: shows a 3D perspective reserve view of the seal membrane in FIG. 12.
Figure 14:
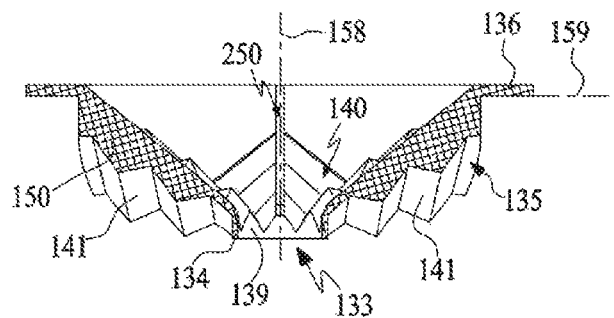
FIG. 14: shows a sectional view along line 14-14 in FIG. 12.
Figure 15:
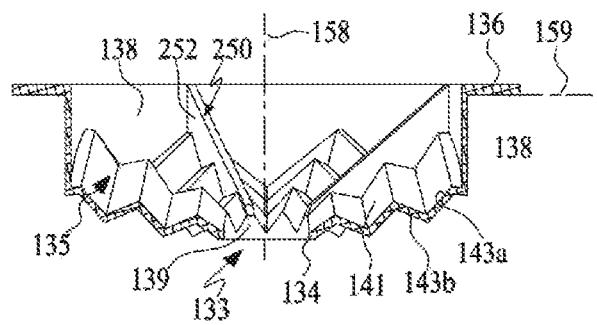
FIG. 15: shows a sectional view along line 15-15 in FIG. 12.
Figure 16:
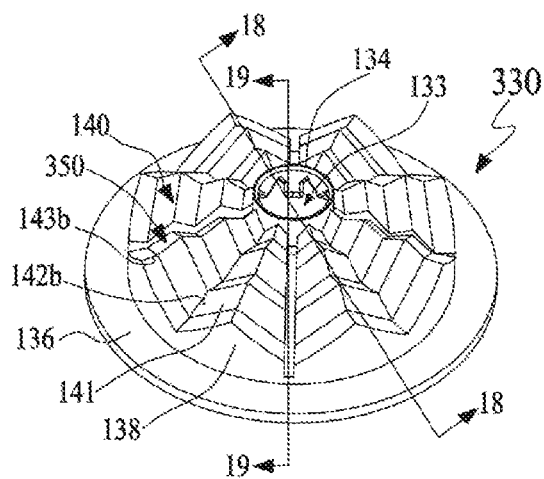
FIG. 16: shows a 3D perspective view of the seal membrane assembly in the third embodiment.
Figure 17:
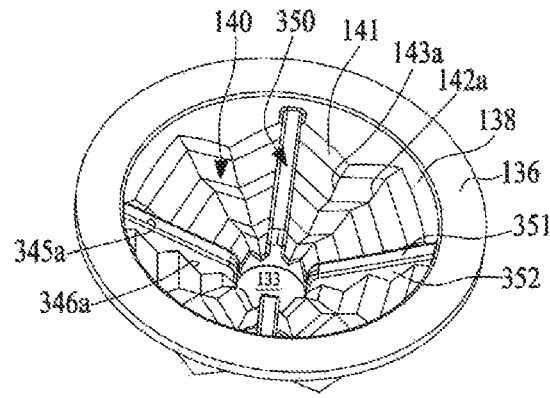
FIG. 17: shows a 3D perspective reserve view of the seal membrane in FIG. 16.
Figure 18:
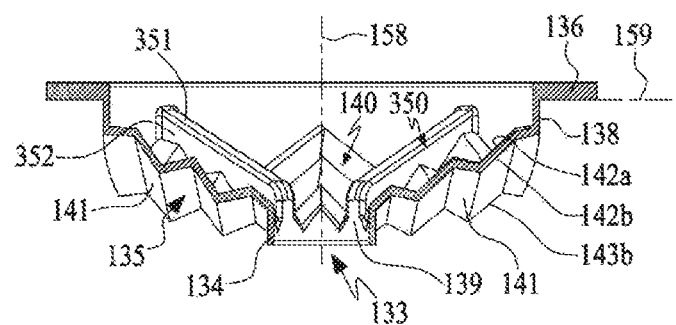
FIG. 18: shows a sectional view along line 18-18 in FIG. 16.
Figure 19:
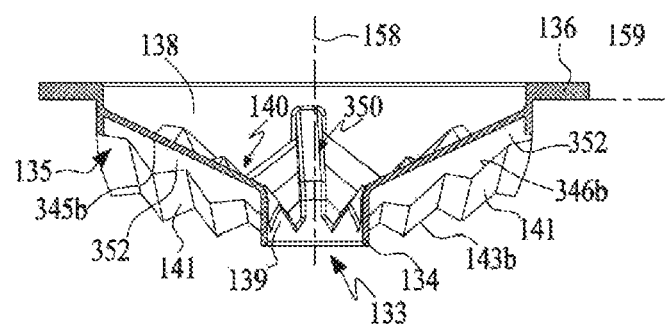
FIG. 19: shows a sectional view along line 19-19 in FIG. 16.
Figure 20:
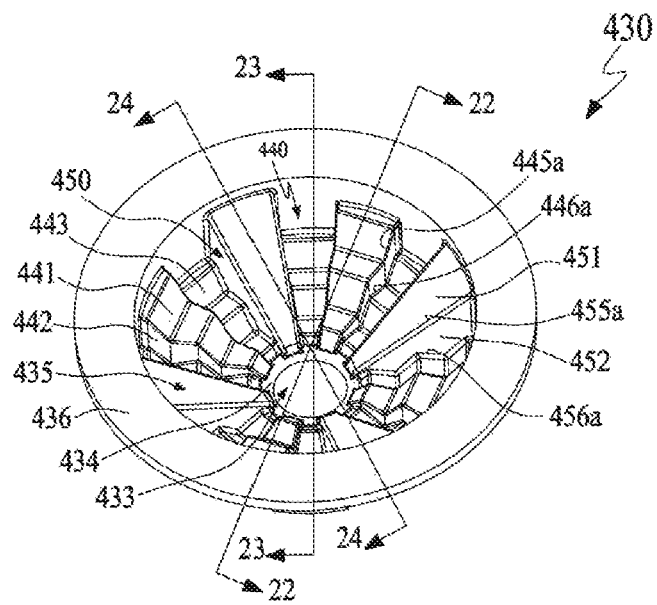
FIG. 20: shows a 3D perspective view of the seal membrane assembly in the forth embodiment.
Figure 21:
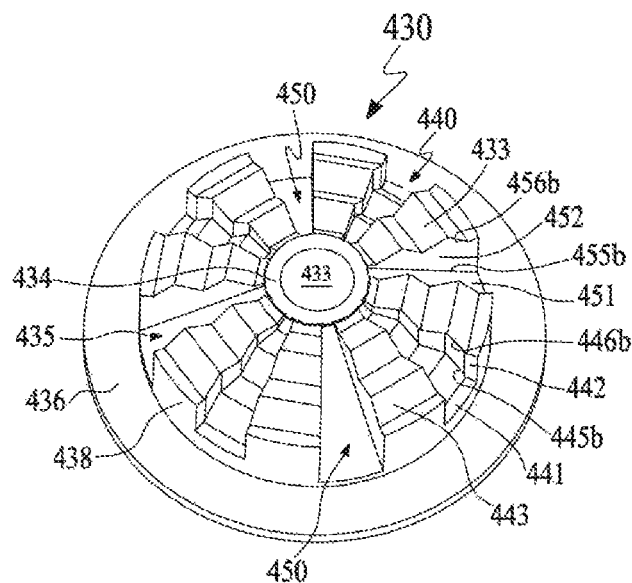
FIG. 21: shows a 3D perspective reserve view of the seal membrane in FIG. 20.
Figure 22:
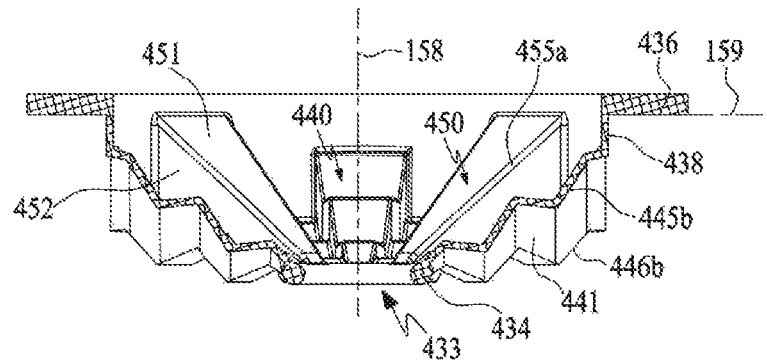
FIG. 22: shows a sectional view along line 22-22 in FIG. 20.
Figure 23:
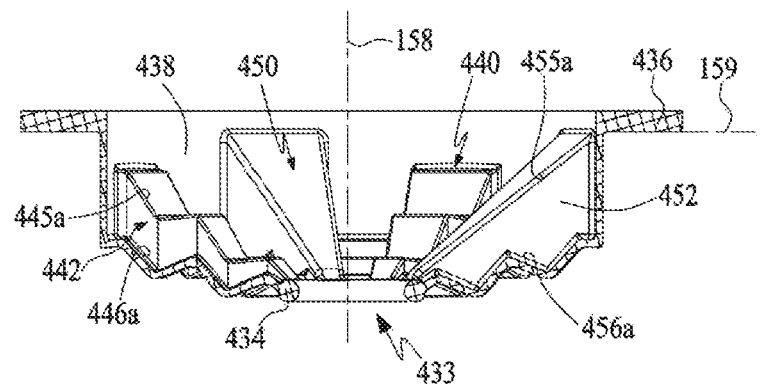
FIG. 23: shows a sectional view along line 23-23 in FIG. 20.
Figure 24:
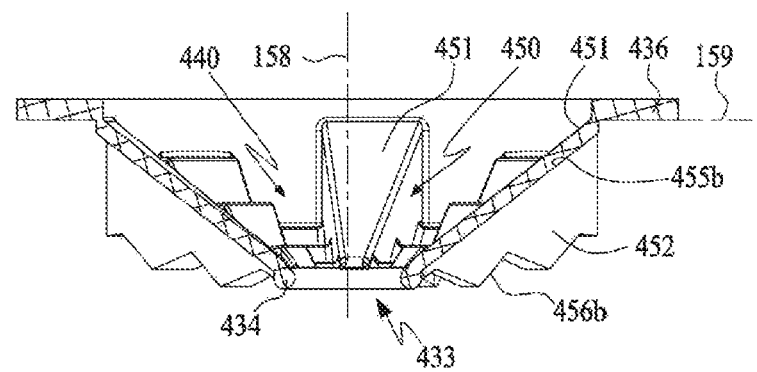
FIG. 24: shows a sectional view along line 24-24 in FIG. 20.
Figure 25:
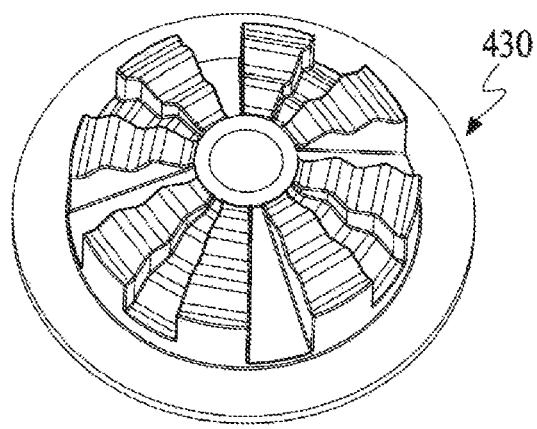
FIG. 25: shows a schematic view of the sealing membrane of FIG. 21 after rounding.

FIG. 6-7 illustrate the composition and assembly relationship of said seal membrane assembly 180, which including a lower retainer ring 120, a seal membrane 130, a protection device 160 and an upper retainer ring 170. Said the seal membrane 130 and said protection device 170 are sandwiched between the lower retainer ring 120 and the upper retainer ring 125, moreover, the cylinder 121 of the said lower retainer ring 120 is aligned with corresponding holes on other components in said seal membrane assembly 180. Said cylinder 121 and the bore 171 of the upper retainer ring 170 are adopted to interference fit, so that the whole seal membrane assembly 180 is in the compressed state. Said protection device 160 includes 4 protectors 163 arranged so as to protect a center sealing body of said seal membrane 130, herein permit the sharp edge of the instrument to pass through without causing perforations or tears to the seal membrane 130.

Said seal membrane 130 includes a proximal opening 132, a distal end aperture 133, and the sealing wall extending from the distal end to the proximal end, said sealing wall including a proximal surface and a distal surface. Said aperture 133 formed by a sealing lip 134 for accommodating an inserted instrument and forming a gas-tight seal. Said sealing lip 134, in the present embodiment, is approximately cylindrical, but said sealing lip 134 may be not circular. As described in the background of the invention, the circumference of the sealing lip should be short and strong enough to ensure sealing reliability when a 5 mm diameter instrument is inserted. In the present embodiment, the sealing lip 334 is circular, defining its radius as Rlip, so that the circumference of the sealing lip is approximately equal to $2*Rlip*\pi(\pi=3.14159)$, usually the circumference of the sealing lip is 0.35~0.5 mm.

Said the seal membrane 130 also including the flange 136; The sealing wall 135 has one end connected to the sealing lip 134 and the other end connected to the flange 136; the floating portion 137 has one end connected to the flange 136 and the other end connected to said proximal end 132. Said flange 136 is for mounting the protector device 160. Said floating portion 137 including one or several plurality of radial (lateral) pleats, so that the entire seal membrane assembly 180 can float in the assembly 200.

Said assembly 180 can be made from a variety of materials with a range of different properties. For instance, said seal membrane 130 is made of a super elastic material such as silicone or polyisoprene; said protector device 160 is made of a semi-rigid thermoplastic elastomer: and said second retainer ring 120 and said first retainer ring 170 are made of a relatively hard rigid material such as polycarbonate.

FIG. 8-11 show more detailed depiction the seal membrane 130 of the first embodiment of the invention. In order to reduce the production cost, the seal membrane 130 is preferably designed as a monolithic part, but can also be designed as an inner seal body and an outer floating portion, separated from the flange 136. The first embodiment is mainly directed to the improvement of the inner seal body. To simplify the description, the outer floating portion and the proximal end are not shown in the subsequent description of the seal membrane.

Said sealing lip 134 comprising a longitudinal axis 158, and a transverse plane 159 that is generally perpendicular to the longitudinal axis 158. Said sealing wall 135 can be approximately frustum, approximately hemispherical, or an irregularly rotating surface. In this embodiment, said wall 135 is formed in an approximately conical arrangement surrounding the sealing lip 134, said wall 135 including a plurality of approximately V-shaped pleats 140. Said pleats 140 and the sealing lip 134 are externally-tangent and extend laterally away from the axis 158. Said pleats 140 include pleat-ridges 142a, 142b; pleat-valley 143a, 143b; and a pleat-wall 141 extending from the pleat-ridge to the pleat-valley. The pleat-ridges 142a, 142b are not straight lines but wavy lines containing peaks and troughs. And the pleat-valley 143a, 143b are not straight lines but wavy lines containing peaks and troughs. The waves of the wavy lines 142a (142b) and 143a (143b) extend laterally in a direction away from the axis 158, referred to as transverse pleats 240 (or radial pleats). The V-shaped pleats 140 generally distribute approximately uniformly around the sealing lip 134, referred to as circumferential pleats (or tangential pleats). Said V-shaped pleats 140 are "multi-dimensional pleats" formed by superposition of transverse pleats and tangential pleats. The sealing lip 134 has a cylindrical portion that intersects the V-shaped pleats 140 to form a proximal side pointing to the tip of triangular wall 139, corresponding to each wave peak 142a (142b).

The advantages of seal membrane 130 with V-shaped pleats 140 thereof, lie in that it can enlarge hoop circumference in the lip-adjacent area, and reduce the hoop force when a large diameter instrument is inserted, thereby reducing the frictional resistance. In this embodiment, 8 pleats are included, while more or less which can enlarge the circumference of the lip-adjacent area. Since said V-shaped pleats 140 are formed by superposition of transverse pleats and circumferential pleats, and the pleats of lip-adjacent area have more degrees of freedom (or smaller constraints of freedom). When a large diameter instrument is inserted into said seal membrane, the sealing wall of the lip-adjacent area deformed and unfolded. The sealing wall outside the lip-adjacent area brings less drag or squeeze, thereby contributing to reduce overall deformation. In addition, the V-shaped pleats 140 contribute to produce less transverse force to the instrument as the instrument moves laterally, thereby benefiting of sealing reliability. However, there is defect in the seal membrane 130 that the axial tensile stiffness of the seal membrane 130 along the sealing lip is small, and it is similar function as a spring when the seal membraned deformed by the tensile force, which causes the stick-slip described in the background to be more obvious.

FIG. 12-15 show more detailed depiction of the seal membrane 230 in the second embodiment. The numerical designations of the geometrical structure in FIG. 12-15 are the same as which in FIG. 8-11, it indicates that the structure of the same designations in the embodiment 2 and the embodiment 1 is basically equivalent. Said seal membrane 230 includes a distal aperture 133, a sealing lip 134, a sealing wall 135 and a flange 136, said the seal membrane 230 including the proximal surface and the distal surface, defining the axis of the sealing lip 134 as the longitude axis 158, and defining the plane which is perpendicular to the longitude axis 158 as the transverse plane 159.

Said wall 135 including a plurality of V-shaped pleats 140 and a plurality of, reinforcing ribs 250. Said V-shaped pleats 140 and the sealing lip 134 are circumscribed and extend laterally away from the axis 158. Said pleats 140 include pleat-ridges 142a, 142b; pleat-valley 143a, 143b; and a pleat-wall 141 extending from the pleat-ridges to the pleat-valley. The pleat-ridges 142a, 142b are not straight lines but wavy lines containing peaks and troughs. And the pleat-valley 143a, 143b are not straight lines but wavy lines containing peaks and troughs. Said V-shaped pleats 140 are "multi-dimensional pleats" formed by superposition of transverse pleats and tangential pleats. The sealing lip 134 has a cylindrical portion that intersects the V-shaped pleats 140 to form a proximal side pointing to the tip of triangular wall 139, corresponding to each wave peak 142a (142b).

The reinforcing rib 250 extends laterally from the sealing lip 134 to the sealing wall-portion 138. In the present embodiment, the reinforcing rib 250 extends laterally along the pleat-ridges, or may extend laterally along the pleat-valley or laterally at an angle to the pleat-ridges (the pleat-valley). In the present embodiment, the reinforcing rib 250 is raised from proximal surface of, said pleats 140 and extends laterally outward to the flange, but may also be raised from the distal surface of the pleats 140 or simultaneously raised from the proximal surface and distal surface. The sidewall 252 of said rib 250 in the embodiment is planar and approximately parallel to the axis 158, but may not be parallel to the axis. The width of the rib 250 in the embodiment is less than the minimum width of one V-shaped pleat 140.

The functions of said reinforcing rib 250 is to drag the sealing lip 134 and its adjacent area. This dragging action enhances the axial tensile stiffness of the entire sealing wall 135. The axial displacement of the sealing lip 134 is small when the instrument is inserted. This embodiment contains 4 reinforcing ribs. More or fewer reinforcing ribs can also play a similar role. The seal membrane 230 with said ribs 250 is provided with the approximate functions similar to which of the seal membrane 130, such as enlarging hoop circumference, reducing the frictional resistance, reducing overall deformation, and reducing transverse force and at the same time contribute to the increased axial stiffness, benefiting of reducing the stick-slip.

Another preferred third embodiment of the seal membrane 330 is described in detail in FIG. 16-19. The numerical designations of the geometrical structure in FIG. 16-19 are the same as which in FIG. 8-11, it indicates that the structure of the same designations in the embodiment 3 and the embodiment 1 is basically equivalent. Said seal membrane 330 includes a distal aperture 133, a sealing lip 134, a sealing wall 135 and a flange 136, said the seal membrane 230 including the proximal surface A and the distal surface B, defining the axis of the sealing lip 134 as the longitude axis 158, and defining the plane which is perpendicular to the longitude axis 158 as the transverse plane 159.

Said wall 135 includes a plurality of V-shaped pleats 140 and a plurality of reverse concave-channels 350 (or hollow convex-ribs 350).

Said V-shaped pleats 140 and the sealing lip 134 are externally-tangent and extend laterally away from the axis 158. Said pleats 140 include pleat-ridges 142a, 142b; pleat-valley 143a, 143b; and a pleat-wall 141 extending from the pleat-ridges to the pleat-valley. The pleat-ridges 142a, 142b are not straight lines but wavy lines containing peaks and troughs. And the pleat-valley 143a, 143b are not straight lines but wavy lines containing peaks and troughs. Said V-shaped pleats 140 are "multi-dimensional pleats" formed by superposition of transverse pleats and tangential pleats. The sealing lip 134 has a cylindrical portion that intersects the V-shaped pleats 140 to form a proximal side pointing to the tip of triangular wall (or trapezoidal surface) 139, corresponding to each wave peak 142a (142b).

A plurality of reverse concave-channels 350 extend laterally outward from the sealing lip 134 to the sealing wall-portion 138. Said reverse concave-channels are recessed from the distal surface of said pleats 140 toward the proximal surface and the opening oriented to the distal surface. From the perspective of the distal surface, said reverse concave-channels 350 are recessed, while from the perspective of the proximal surface, the reverse concave-channels 350 are hollow convex-ribs raised from the sealing body. Said reverse concave-channels 350 include an inner-sealing-wall 351, a side-sealing-wall 352. The inner-sealing-wall 351 intersects side-sealing-wall 352 to form an intersection line 355a, 355b; said side-sealing-wall 352 intersects the pleat-wall to form an intersection line 356a, 356b. The inner-sealing-wall 351 and one end of the side-sealing-wall 352 intersects the sealing lip 134 and the other end intersects the sealing wall-portion 138. The seamless sealing wall is formed by a plurality of V-shapes pleats 140 and a plurality of the reverse concave-channels 340. In the present embodiment, there are 8 V-shaped pleats 140 and 4 reverse concave-channels 350, however more or fewer pleats or reverse concave-channels can be used. The side-sealing-wall 352 of said reverse concave-channels is a plane side-wall without pleats and its function equivalent to the reinforcing rib 250 described in the second embodiment. The inner-sealing-wall 351 is also planar in the present embodiment, however the inner-sealing-wall may also be a pleated curved surface.

Said V-shaped pleats 140 and reverse concave-channels 350 together enlarge hoop circumference in the lip-adjacent area; said V-shaped pleats 140 can reduce overall deformation of the sealing lip; while reverse concave-channels 350 can drag the sealing lip 134 and the lip-adjacent area. This dragging action enhances the axial tensile stiffness of the entire sealing wall 135. The axial displacement of the sealing lip 134 is small when the instrument is inserted. Therefore, said seal membrane 330 has the functions of enlarging hoop circumference, reducing overall deformation and transverse force, increasing the axial tensile stiffness, reducing the frictional resistance, and improving stick-slip and sealing reliability.

FIG. 20-25 depict the seal membrane 230 of the fourth embodiment in the invention. Said seal membrane 430 includes a distal aperture 433, a sealing lip 434, a sealing wall 435 and a flange 436, said distal aperture 433 formed by the sealing lip 434. Said sealing wall 435 connects the sealing lip 434 at one end and connects the sealing wall-portion 438 of the flange 436 at the other end, said the seal membrane 430 including the proximal surface and the distal surface, defining the axis of the sealing lip 434 as the longitude axis 158, and defining the plane which is perpendicular to the longitude axis 158 as the transverse plane 159.

Said wall 435 includes a plurality of U-shaped pleats 440 and a plurality of reverse concave-channels 450 (or hollow convex-ribs 450).

Said U-shaped pleats 440 and the sealing lip 434 are externally-tangent and extend laterally outside. Said U-shaped pleats 440 include inner pleat-wall 441, outer pleat-wall 443 and pleated sidewall connecting said inner pleat-wall 441 and outer pleat-wall 443. The inner pleat-wall 441 intersects said pleated side-sealing-wall 442 to form an intersection line 445a, 445b; said outer pleat-wall 443 intersects the pleated side-sealing-wall 442 to form an intersection line 446a, 446b. Said line 445a (445b) and said line 446a (446b) are not straight lines but wavy lines containing peaks and troughs. The waves of the wavy lines 445a (445b) and 446a (446b) extend laterally in a direction away from the axis 458, referred to as transverse pleats 240 (or radial pleats). The U-shaped pleats 440 generally distribute approximately uniformly around the sealing lip 434, referred to as tangential pleats (or circumferential pleats). Said U-shaped pleats 440 are "multi-dimensional pleats" formed by superposition of transverse pleats and tangential pleats.

A plurality of reverse concave-channels 450 extends from the sealing lip 434 laterally outward to the sealing wall portion 438. Said reverse concave-channels 450 recess from the distal surface of said pleats 440 toward the proximal surface. While from the perspective of the proximal surface, the reverse concave-channels 450 are hollow convex-ribs raised from the sealing body. Said reverse concave-channels 450 include an inner-sealing-wall 451, a side-sealing-wall 452. The inner-sealing-wall 451 intersects side-sealing-wall 452 to form an intersection line 455a, 455b; said side-sealing-wall 452 intersects the pleat-wall 113 to form an intersection line 456a, 456b. The inner-sealing-wall 451 and one end of the side-sealing-wall 452 intersects the sealing lip 434 and the other end intersects the sealing wall-portion 438. The seamless sealing wall is faulted by a plurality of U-shapes pleats 440 and a plurality of the reverse concave-channels 450. In the present embodiment, there are 8 V-shaped pleats 440 and 4 reverse concave-channels 450, however more or fewer pleats or reverse concave-channels can be used. The side-sealing-wall 452 of said reverse concave-channels 450 is a plane side-wall without pleats and its function is equivalent to the reinforcing rib 250 described in the second embodiment. The inner-sealing-wall 451 is also planar in the present embodiment, however the inner-sealing-wall may also be a pleated curved surface.

Said U-shaped pleats 440 and reverse concave-channels 450 together enlarge hoop circumference in the lip-adjacent area; said U-shaped pleats 440 can reduce overall deformation of the sealing lip; while reverse concave-channels 450 can stretch the sealing lip 434 and its adjacent area. This stretching action enhances the axial tensile stiffness of the entire sealing wall 435. The axial displacement of the sealing lip 434 is small when the instrument is inserted. Therefore, said seal membrane 430 has the functions of enlarging hoop circumference, reducing overall deformation and transverse force, increasing the axial tensile stiffness reducing the frictional resistance, and improving stick-slip and sealing reliability.

Those skilled in the art easily understand that the reasonable fillet transition can avoid stress concentration or make certain areas deformed more easily. Due to the small size of the seal membrane, especially the area near the sealing lip is smaller, with such a small size and different chamfer, the shape of the seal membrane looks different. In order to clearly show the geometric relationship of the elements, the embodiment of the invention is generally the pattern without the fillet.

Many different embodiments and examples of the invention have been shown and described.

One ordinary skilled in the art will be able to make adaptations to the methods and apparatus by appropriate modifications without departing from the scope of the invention. The structure and the fixing manner of the protector assembly disclosed in U.S. Pat. No. 7,788,861 are used in the embodiments of the present invention. While the structure and the fixing manner of the protector assembly disclosed in U.S. Pat. No. 7,988,671 can be used; and in some applications, the protector assembly may not be included. The approximate U-shaped concave-furrows and the approximate V-shaped concave-furrows described in this embodiment cannot be limited to U-shaped or V-shaped. It has been mentioned many times in the invention that the concave-furrow extends laterally outward from the sealing lip, and the so-called "extending laterally outward" should not be limited to a straight line. Said "extending laterally outward" can be a spiral, a line segment, a multi-section arc line and so on. In the invention, the positional relationship of the intersecting surfaces composed of said concave-furrow and the intersection line thereof are described with reference to specific embodiments, and the methods of increasing curved surfaces to form a multifaceted mosaic or using of the high-order curved surface to make the intersection line and the concave-furrow shape to look different from said embodiment. However, it can be considered not deviated from the scope of the invention, as long as it conforms to the general idea of the invention. Several modifications have been mentioned, to those skilled in the art, other modifications are also conceivable. Therefore, the scope of the invention should follow the additional claims, and at the same time, it should not be understood that it is limited by the specification of the structure, material or behavior illustrated and documented in the description and drawings.

I claim:

1. A trocar seal membrane for minimally invasive surgery, comprising: a proximal opening, a distal aperture, and a sealing wall from the distal aperture extending to the proximal opening, wherein the sealing wall comprises a proximal surface and a distal surface; the distal aperture formed by a sealing lip for accommodating an inserted instrument forms a gas-tight seal; the sealing wall simultaneously has a plurality of transverse pleats extending laterally outward from the sealing lip and a plurality of tangential pleats uniformly distributed around the sealing lip; and a superposition of the transverse pleats and the tangential pleats form multi-dimensional pleats;

wherein the sealing wall further comprises a plurality of reverse concave-channels extending laterally outward from the sealing lip and recessing from the distal surface of the sealing wall to the proximal surface, the opening of reverse concave-channels towards the distal surface; and from the perspective of the proximal surface, each of the plurality of reverse concave-channels is a hollow convex-rib raised from the proximal surface.

2. The seal membrane according to claim 1, wherein the multi-dimensional pleats increase the degrees of freedom of the sealing wall in a lip-adjacent area which has a benefit of reducing overall deformation.

3. The seal membrane according to claim 1, wherein the number of the reverse concave-channels is four.

4. The seal membrane according to claim 1, wherein the sealing lip is circular or cylindrical.

5. The seal membrane according to claim 1, wherein each of the plurality of reverse concave-channels comprises two plane side-walls without pleats.

6. The seal membrane according to claim 5, wherein the plane side-walls are configured to enlarge hoop circumference in a lip-adjacent area and increase the axial tensile stiffness.

7. The seal membrane according to claim 5, wherein the seal membrane further comprises a flange that intersects the multi-dimensional pleats and the reverse concave-channels simultaneously, and a floating portion with a plurality of transverse pleats extending from the flange to the proximal opening.

8. The seal membrane according to claim 1, wherein the sealing wall further comprises a solid-rib extending laterally outward from the sealing lip; the solid-rib is configured to enhance the axial tensile stiffness of the sealing wall and improve stick-slip.

9. The seal membrane according to claim 8, wherein the seal membrane further comprises a flange that intersects the pleats and the solid-rib simultaneously, and a floating portion with a plurality of transverse pleats extending from the flange to the proximal opening.

10. The seal membrane according to claim 1, wherein the sealing wall is formed in an approximately conical arrangement surrounding the sealing lip, and each of the plurality of transverse pleats includes a pleat-ridge and a pleat-valley, and a pleat-wall extending from the pleat-ridge to the pleat-valley; the pleat-ridge containing peaks and troughs, and the pleat-valley containing peaks and troughs.

11. The seal membrane according to claim 10, wherein each of the plurality of reverse concave-channels comprises two plane side-walls without pleats.

12. The seal membrane of claim 11, wherein, the plane side-walls are configured to enlarge hoop circumference in a lip-adjacent area and increase the axial tensile stiffness.

13. The seal membrane of claim 12, wherein the number of the the reverse concave-channels is four.

* * * * *